United States Patent [19]

Bodor et al.

[11] 4,000,132
[45] Dec. 28, 1976

[54] METHOD FOR SYNTHESIZING CERTAIN SELECTED PRO-DRUG FORMS OF THEOPHYLLINE

[75] Inventors: Nicolae S. Bodor; Kenneth B. Sloan; Yu-Neng Kuo, all of Lawrence, Kans.

[73] Assignee: Interx Research Corporation, Lawrence, Kans.

[22] Filed: Nov. 22, 1974

[21] Appl. No.: 526,219

[52] U.S. Cl. .......................... 260/240 J; 260/256
[51] Int. Cl.[2] ................................ C07D 473/08
[58] Field of Search .................. 260/256, 240 J

[56] References Cited
UNITED STATES PATENTS 2,729,643   1/1956   Stoll et al. ................ 260/256

Primary Examiner—Paul M. Coughlan, Jr.
Attorney, Agent, or Firm—John J. McDonnell

[57] ABSTRACT

There is provided, a method for synthesizing certain selected pro-drug forms of theophylline, having the formula:

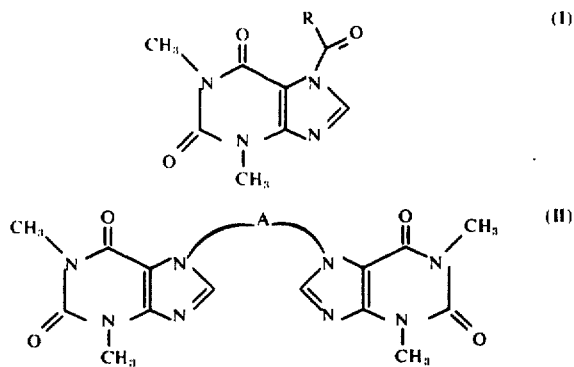

wherein R represents a member selected from the group consisting of a straight or branched $C_4-C_{20}$ alkyl group, a straight or branched $C_4-C_{20}$ alkenyl group, a substituted phenyl group or a substituted or unsubstituted naphthyl group whose substituents are selected from the group consisting of a hydroxy group, a $C_1-C_4$ alkyl group, a $C_1-C_4$ alkoxy group, a $C_1-C_4$ acyloxy group, and a halogen atom and a substituted or unsubstituted heteroaromatic group whose substituents are selected from the group consisting of a hydroxy group, a $C_1-C_4$ alkyl group, a $C_1-C_4$ alkoxy group, a $C_1-C_4$ acyloxy group, and a halogen atom, and wherein A represents a member selected from the group consisting of a —CO— group, a —CO—$(CH_2)_n$—CO— group, wherein $n$ represents an integer of from 1 to 16, a —CO—CH=CH—CO— group (cis or trans) a

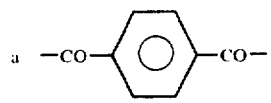

group and a

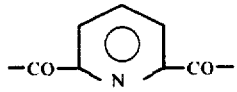

group, which comprises:

Reacting theophylline with an appropriate acid in the presence of dimethylformamide, $COCl_2$ or $SOCl_2$, organic tertiary or aromatic amine base or inert carrier gas for removing HCl, and suitable solvent. The compounds prepared by this process are useful for treating asthma by releasing theophylline in sustained manner.

9 Claims, No Drawings

METHOD FOR SYNTHESIZING CERTAIN SELECTED PRO-DRUG FORMS OF THEOPHYLLINE

BACKGROUND OF THE INVENTION

1. FIELD OF THE INVENTION

The present invention is directed to a method for preparing certain selected pro-theophylline derivatives. More particularly, the present invention is directed to a method for preparing certain "pro-drug" forms of theophylline useful in the treatment of asthma in warm-blooded animals, e.g., humans.

The compounds prepared by the method of this invention are described in pending patent application, Ser. No. 463,092, filed Apr. 22, 1974, and entitled "USEFUL PRO-DRUG FORMS OF THEOPHYLLINE," the subject matter of which is incorporated herein by reference.

2. DESCRIPTION OF THE PRIOR ART

Theophylline, normally administered as the ethylenediamine salt (Aminophylline) or choline salt, is a useful and potent bronchodilator commonly prescribed for the treatment of bronchial asthma. Because it is readily soluble, Aminophylline has for many years been accepted as an effective bronchodilator when given orally. However, Aminophylline in solution becomes highly alkaline and is hydrolized by the gastric juice with resultant gastric irritation from the free theophylline liberated.

5 to 12 mcg./ml of whole blood or 10 to 25 mcg./ml of plasma are the relative blood levels of theophylline generally accepted as necessary to achieve effective bronchodilation. See, E. G. Truitt, V. A. McKusick, J. C. Krantz, Jr., Pharm. Exp. Ther., 100, 309 (1950) and M. Warwick Turner, Brit. Med. Jr., 2, 67 (1957), respectively. These theophylline blood levels are, however, difficult to attain, since as a result of the gastrointestinal upset experienced, patients cannot tolerate an adequate therapeutic dose of the drug. Reports in the literature with a variety of theophylline derivatives have often shown not only that theophylline blood levels achieved are below the values required for the relief of a bronchospasm, but also that even when these therapeutic levels are obtained, they fall off extremely rapidly in the first few hours following administration of the drug. Thus, repeated dosing of the patient about every 3 to 4 hours is necessary. See, E. G. Truitt, V. A. McKusick, J. C. Krantz, Jr., and M. Turner-Warwick, and R. H. Jackson, J. I. McHenry, S. B. Moreland, W. J. Raymer, and R. L. Etter, Dis. Chest., 45, 75 (1964), and J. Schluger, J. T. McGuinn, and D. J. Hennesey, Amer. J. Med. Sci. 233, 296 (1957), respectively.

In addition, even when therapeutic blood levels of theophylline are achieved, the amount of theophylline administered to a patient is so excessive that the therapeutic blood level achieved approaches and often reaches toxicity.

In one attempt to overcome the above disadvantages associated with administering theophylline, certain individuals have prepared a continuous-release formulation, such that the release rate of theophylline is dependent upon the formulation medium into which it is incorporated. That is, sustained therapeutic blood levels of theophylline are achieved through the use of a particular pharmaceutical formulation rather than chemical modification of the theophylline molecule. See, C. Boroda, R. B. Miller, S. T. Leslie, E. G. Nicol and I. Thompson, Clin. Pharm., 383 (1973) and D. McIntosh, Brit. J. Clin. Pharm., 12, 233 (1971) respectively.

Some theophylline derivatives, analogous to the compounds of formula (I) described hereinabove, have been prepared and described in the literature for the purpose of studying their chemistry per se, without any indication of any pharmaceutical utility. For instance, 7-acetyltheophylline was reported in three different articles. See, for instance, T. Higuchi, H. K. Lee and Ian H. Pittman; Farm. Aikak. 80, 55 (1971) and Y. Ishido, A. Hosono, S. Isome, A. Maruyama, and T. Sato, Bull. Chem. Soc. Japan, 37, 1389 (1964), respectively.

7-acetyltheophylline and 7-benzoyltheophylline were reported in H. Biltz, and K. Struffe, Ann., 404, 170 (1914) as well.

7-propionyltheophylline and 7-butyryltheophylline have also been reported in the literature. See, Y. Ishido, A. Hosono, S. Isome, A. Maruyama, and T. Sato, supra.

Finally, United States Pat. No. 2,729,643 discloses certain 7-carboxamidotheophylline derivatives useful as diuretics.

As for the compounds of formula (II) described herein above, no prior art of structural chemical or pharmacological significance is known.

United States Patent Application, Ser. No. 463,092 ('092), referred to earlier, describes a basic synthesis scheme for preparing the compounds encompassed by formulas (I) and (II) of this Application. See, page 7, line 2 through page 8, line 33 of the '092 application, inclusive.

Admittedly, while all the compounds encompassed within formulas (I) and (II) of this invention can be prepared by the synthesis scheme described in the '092 application, such compounds are deficient from the standpoint of (1) substantial purity, and, moreover, (2) substantial stability. Furthermore, the synthesis scheme disclosed in the '092 application is quite expensive, especially from the standpoint of commercial acceptance and exploitation.

Therefore, it is readily apparent that a need exists for a means to inexpensively prepare the compounds of formula (I) and (II) in a more (1) pure and (2) stable form.

SUMMARY OF THE INVENTION

It is, therefore, one object of the present invention to prepare the compounds of formula (I) and (II) (hereinafter described) in substantially pure form.

It is another object of the present invention to prepare the above-identified compounds in a substantially stable form.

Finally, it is still another object of the present invention to prepare the above-described compounds inexpensively so as to make production of the same commercially feasible and acceptable.

To the above extent, all the foregoing objects are achieved with the method hereinafter described.

Compounds of the formula:

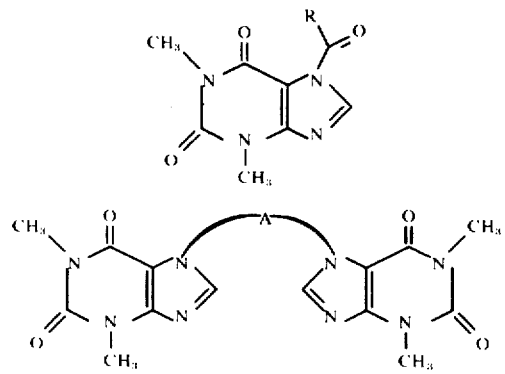

wherein R represents a member selected from the group consisting of a straight or branched $C_4$–$C_{20}$ alkyl group, a straight or branched $C_4$–$C_{20}$ alkenyl group, a substituted phenyl group or a substituted or unsubstituted naphthyl group whose substituents are selected from the group consisting of a hydroxy group, a $C_1$–$C_4$ alkyl group, a $C_1$–$C_4$ alkoxy group, a $C_1$–$C_4$ acyloxy group, and a halogen atom and a substituted or unsubstituted heteroaromatic group whose substituents are selected from the group consisting of a hydroxy group, a $C_1$–$C_4$ alkyl group, a $C_1$–$C_4$ alkoxy group, a $C_1$–$C_4$ acyloxy group, and a halogen atom, and wherein A represents a member selected from the group consisting of a —CO— group, a —CO—$(CH_2)_n$—CO— group, wherein $n$ represents an integer of from 1 to 16, a —CO—CH=CH—CO— group (cis or trans), a

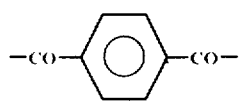

group, and a

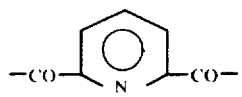

group, are conveniently prepared by:

1. Reacting stoichiometric amounts of theophylline with a member selected from the group consisting of the corresponding R-mono-carboxylic acid or anhydride or A-dicarboxylic acid or anhydride, wherein R and A are defined as above, in the presence of:
  a. a stoichiometric amount of dimethylformamide,
  b. a solvent selected from the group consisting of a conventional halogenated hydrocarbon solvent (e.g., dichloromethane, dichloroethane, chloroform, etc.) or a mixture of said halogenated hydrocarbon solvent with any conventional hydrocarbon solvent (e.g., hexane, heptane, octane, benzene, toluene, xylene, etc.), and/or dimethylformamide,
  c. a member selected from the group consisting of an inert gas (e.g., nitrogen, helium, purified methane) and an organic tertiary or aromatic amine base (e.g., trimethylamine, triethylamine, pyridine, methylimidazole, quinoline, quinuclidine, 2,2-diazabicyclo [2.2.2] octane, etc.), and
  d. a slight excess of a member selected from the group consisting of phosgene ($COCl_2$) and thionyl chloride ($SOCl_2$) to yield the desired pro-theophylline compound, said member of (d) being present in an amount of from 1.0 to 1.5 equivalents per carboxylic molecule and 1.0 to 2.0 equivalents per anhydride molecule, and 2. Separating the thus obtained pro-theophylline compound from the reaction mixture, said reaction being carried out in an anhydrous environment at a temperature ranging from 0° to 120° C (but preferably at the boiling point of the solvent or solvent mixture employed), standard pressure and for a period ranging from 1 to 72 hours (preferably, however, 20 to 48 hours).

In the above reaction scheme, the theophylline goes into solution and as the reaction proceeds, the desired pro-theophylline compound will crystallize out of the reaction mixture. Consequently, once the final product is separated from the reaction mixture, it is in an essentially purified and stable state. However, if it becomes necessary, the final obtained product can be further purified via trituration with a hot conventional halogenated hydrocarbon as described above. Optionally, the acylated pro-theophylline compounds can be purified via recrystallization with a conventional hydrocarbon solvent as noted earlier.

The inert gas or organic tertiary or aromatic amine base serves as a carrier or as a scavenger, respectively, and removes any HCl formed during the reaction. Any inert gas is permissible, and those provided above are typical.

While any conventional aliphatic or aromatic hydrocarbon solvent is operable in the above-described process, the best results have been obtained using solvents of the latter type.

In addition to the foregoing, it is extremely important to note that the above-described reaction mixture must absolutely be protected from humidity. This can be done by simply carrying out the above-described reaction in the presence of a conventional drying tube(s) containing any conventional dessicant such as calcium chloride.

The advantages of the above-described process are three-fold. Firstly, the pro-theophylline compound so prepared is of substantial purity; secondly, the pro-theophylline compound so prepared is of substantial stability; and finally, the overall process is much less expensive than that described in the '092 application, thus enabling these pro-theophylline compounds to be more readily acceptable on a commercial scale. All three advantages stem from the use of (1) $COCl_2$ or $SOCl_2$ during the reaction, (2) substitution of a mono- or di-carboxylic acid or anhydride for the acyl chloride employed in the synthesis described in the '092 application, and (3) the presence of the dimethylformamide.

Without further elaboration, it is believed that one of ordinary skill in the art can, using the preceding description, utilize the present invention to its fullest extent. Accordingly, the following preferred specific embodiments are, therefore, to be construed as merely illustrative and not limitative of the remainder of the specification and claims in any way whatsoever.

EXAMPLE I

PREPARATION OF 7,7'-SUCCINYLDITHEOPHYLLINE (PER '092 APPLICATION)

9.0 g (0.05 mole) of grounded theophylline was suspended in about 1 liter of anhydrous $CHCl_3$. The mixture was then cooled to $-20°$ to $-40°$ C (dry ice - 1,2-dichloroethane bath). Next, 3.8 g (0.0247 mole) of succinyl chloride was then added to the initial solution. 5 ml (0.062 mole) of pyridine, diluted in 50 ml of $CHCl_3$ was then added dropwise to the resulting solution. The solution was then stirred and maintained at a temperature of from $-20°$ to $-40°$ C for a period of from 4 to 6 hours to give a white crystalline final product in essentially quantitative yield (90–95% yield). The final product was then filtered and washed with anhydrous $CHCl_3$ (3 × 300 ml) to give an essentially quantitative yield of the final product, Mp 266° C.

Anal. Calc'd for $C_{18}H_{18}N_8O_6$: C, 48.87; H, 4.10; N, 25.33. Found: C, 48.44; H, 4.19; N, 25.77.

EXAMPLE II

PREPARATION OF 7,7'-SUCCINYLDITHEOPHYLLINE ($COCl_2$ APPROACH, THIS INVENTION)

To a 3-neck, 3 liter flask equipped with a dropping funnel, condenser and mechanical motor stirrer, N,N-dimethylformamide (250 ml, 3.39 moles) was added. Then, 250 ml (0.315 mole) of $COCl_2$ (12.5% in benzene or toluene) was added slowly from the dropping funnel. After the $COCl_2$-benzene (toluene) solution was completely added, 25 g (0.25 mole) of succinic anhydride was added, followed by 1.5 liters of dichloromethane ($CH_2Cl_2$), after which 90 g (0.5 mole) of theophylline was added. Next, pyridine (40 g, 0.5 mole) in 100 ml of dichloromethane was added. The solution was heated under reflux for 20 hours and the precipitate thus formed was filtered while the solution was hot. The filtered precipitate was then heated under reflux with 1 liter of dichloromethane for 2 to 4 hours. The precipitate was filtered and dried to give 88 g (80%) of the desired product. Mp 266°–268° C.

Anal. Calc'd for $C_{18}H_{18}N_8O_6$: C, 48.87; H, 4.10; N, 25.33. Found: C, 48.70; H, 3.91; N, 25.61.

EXAMPLE III

PREPARATION OF 7,7'-SUCCINYLDITHEOPHYLLINE ($SOCl_2$ APPROACH, THIS INVENTION)

(1) To 2.03 g (17.0 mmole) of $SOCl_2$ there was added 2.77 g (38.0 mmole) of dimethylformamide and 0.83 g (7.0 mmole) of succinic acid, in that order, at room temperature while nitrogen was bubbled through the reaction mixture; the reaction became warm but not excessively during the addition of the dimethylformamide. Then, 2.52 g (14.0 mmole) of theophylline was added and the resulting white suspension was diluted with 100 ml of dichloromethane. Finally, 2.82 g (34 mmole) of pyridine was added dropwise to the well-stirred suspension causing the suspension to gradually clear and the resulting solution to take on a yellow color. All the additions were done at room temperature and nitrogen was bubbled through the reaction mixture the entire time. The reaction solution was then protected from atmospheric moisture with a calcium chloride drying tube, and it was refluxed overnight with the heating bath temperature at 60°–70° C. The resulting suspension was filtered and the residue was washed with dichloromethane to give 1.50 g (50% yield) of 7,7'-succinyldithephylline as a white solid whose infrared and ultraviolet spectra showed no theophylline impurity. The infrared spectrum of the compound was characterized by three bands at 3060 $cm^{-1}$ (m)(N-CH=N), 1745 $cm^{-1}$ (s)(N-C=O) and 1540 $cm^{-1}$ (m) while theophylline itself showed a very broad intense absorption between 3300–2200 $cm^{-1}$ in which it is difficult to pick out a characteristic absorption; did not show any absorption at 1745 $cm^{-1}$ and showed that the 1540 $cm^{-1}$ absorption shifted to 1570 $cm^{-1}$. The ultraviolet spectrum of the compound in dichloromethane is characterized by a symmetrical band centered at 300 m$\mu$ with an intensity of $\epsilon = 1.31 \times 10^4$, while theophylline is characterized by a symmetrical band centered at 270 m$\mu$ with an intensity of $1.0 \times 10^4$.

Anal. Calc'd for $C_{18}H_{18}N_8O_6$: C, 48.87; H, 4.10; N, 25.33. Found: C, 49.19; H, 4.11; N, 25.02.

2. To 1.89 g (15.9 mmole) of well-stirred $SOCl_2$ at room temperature was added 2.60 g (35.6 mmole) of dimethylformamide, dropwise, and 0.80 g (8 mmole) of succinic anhydride. The resulting suspension was stirred at room temperature for 1 hour during which time it became homogeneous and light yellow in color. Then dichloromethane (50 ml) was added to the solution followed by 2.70 g (15 mmole) of theophylline, 50 ml of dichloromethane and 2.80 g (35.4 mmole) of pyridine. Nitrogen was bubbled through the suspension for 20 minutes and then it was refluxed overnight in a reaction flask equipped with a calcium chloride drying tube to protect it from atmospheric moisture; the suspension became homogeneous after about 1 hour at reflux. The next day the resulting suspension was filtered while hot to give 1.70 g (51% yield) of 7,7'-succinyldithephylline as a white solid: infrared identical with that of 7,7'-succinyldithephylline from example (1) above; uv ($CH_2Cl_2$) $\lambda_{max}^{300}$ $\epsilon = 1.30 \times 10^4$.

Anal. Calc'd for $C_{18}H_{18}N_8O_6$: C, 48.87; H, 4.10; N, 25.33. Found: C, 48.79; H, 4.08; N, 25.63.

In similar fashion, by using the appropriate generic and/or specifically described reactants and/or operating conditions described above, the following additional compounds can be obtained:

1. 7-hexanoyltheophylline
2. 7-octanoyltheophylline
3. 7-decanoyltheophylline
4. 7-dodecanoyltheophylline
5. 7-myristyltheophylline
6. 7-palmityltheophylline
7. 7-stearyltheophylline
8. 7-[2-hydroxy]-benzoyltheophylline
9. 7-[2-acetyloxy]-benzoyltheophylline
10. 7,7'-carbonylditheophylline
11. 7,7'-succinylditheophylline
12. 7,7'-terephthaloylditheophylline
13. 7,7'-fumaroylditheophylline
14. 7,7'-glutarylditheophylline
15. 7,7'-adipylditheophylline

EXAMPLE IV

COMPARISON OF THE STABILITY OF 7,7'-SUCCINYLDITHEOPHYLLINE OBTAINED BY THE METHOD OF THIS INVENTION AS COMPARED TO THE METHOD DESCRIBED IN THE '092 APPLICATION

In order to determine the stability of 7,7'-succinyldi-theophylline as prepared by the instant invention and as prepared by the '092 application, the characteristic UV extinction was followed at 300 nm. Although at time 0 no superficial difference in the batches prepared could be detected by the usual analytical procedures (elementary analysis, U.V., I.R., M.P.), the compound obtained from the method described in the '092 application using succinyl chloride was demonstrated to be far inferior from the point of stability as compared to the same compound prepared by the method of this invention using either $SOCl_2$ or $COCl_2$. This is readily apparent when one reviews the results set forth in Table I below:

TABLE I

| Batch Identification | Preparation | *$CH_2CH_2$ $\epsilon$max × 10³ | Conditions for Stability Studies 60° C, Closed Ampules | | | | | |
|---|---|---|---|---|---|---|---|---|
| | | | One Week | | Two Weeks | | Three Weeks | |
| | | | $CH_2CH_2$ $\epsilon$max × 10³ | %** | $CH_2CH_2$ $\epsilon$max × 10³ | %** | $\epsilon$max × 10³ | %** |
| KBS-337,75 | A | 1.30 | 0.948 | 72.8 | 0.710 | 54.6 | — | — |
| KBS-356,97 | B | 1.30 | 1.28 | 98.5 | 1.21 | 93.5 | 1.16 | 89.5 |
| K-152 | C | 1.30 | 1.25 | 94.0 | — | — | 1.12 | 86.0 |

A - '092 Application using succinyl chloride
B - This Application using $SOCl_2$
C - This Application using $COCl_2$
* - time zero
** - purity The preceding examples can be repeated with similar success by substituting the generically or specifically described reactants and/or operating conditions of this invention for those used in the preceding example.

The pro-drug forms obtained by the process of this invention are suitably administered in oral dosage form, such as by tablet or capsule, by combining the same in a therapeutic amount with any oral pharmaceutically acceptable inert carrier, such as lactose, starch (pharmaceutical grade), dicalcium phosphate, calcium sulfate, Kaolin, Mannitol, and powdered sugar. In addition, when required, suitable binders, lubricants, disintegrating agents, and coloring agents can also be added. Typical binders include starch, gelatin, sugars, such as sucrose, molasses, and lactose, natural and synthetic gums such as acacia, sodium alginate, extract of Irish moss, carboxymethylcellulose, methylcellulose, and polyvinylpyrrolidone, polyethylene glycol, ethylcellulose and waxes. Typical lubricants for use in these dosage forms can include, without limitation, boric acid, sodium benzoate, sodium acetate, sodium chloride, leucine, and polyethylene glycol. Suitable disintegrators can include, without limitation, starch, methylcellulose, agar, bentonite, cellulose and wood products, alginic acid, guar gum, citris pulp, carboxymethylcellulose, and sodium lauryl sulfate. If desired, a conventionally pharmaceutically acceptable dye can be incorporated into the dosage unit form, i.e., any of the standard FD&C dyes.

Any skilled artisan can prepare these oral dosage forms by simply referring to the oral dosage form preparatory procedure outlined in "REMINGTON'S PHARMACEUTICAL SCIENCES," Fourteenth Edition (1970), pages 1659 through 1698 inclusive.

While the therapeutic dosage range for the compounds of this invention will vary with the size and needs of the patient, generally speaking, therapeusis on a daily basis is achieved by administering 10 mg. to 15 mg. per Kg. of body weight, about every 8 to 12 hours.

From the foregoing description, one of ordinary skill in the art can easily ascertain the essential characteristics of this invention, and without departing from the spirit and scope thereof, can make various changes and modifications of the invention to adapt it to various usages and conditions. As such, these changes and modifications are properly, equitably, and intended to be, within the full range of equivalence of the following claims.

We claim:

1. A method for preparing a pro-drug form of theophylline having the formula:

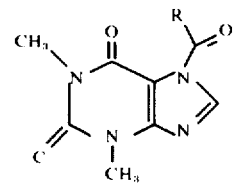

(I)

or

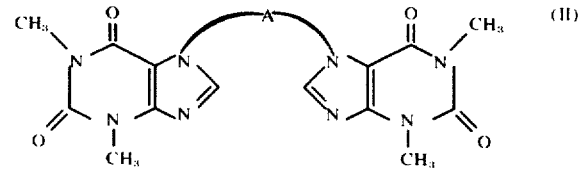

(II)

wherein R represents a member selected from the group consisting of straight or branched $C_4$-$C_{20}$ alkyl, straight or branched $C_4$-$C_{20}$ alkenyl, substituted phenyl or a substituted or unsubstituted naphthyl whose substituents are selected from the group consisting of hydroxy, $C_1$-$C_4$ alkyl, $C_1$-$C_4$ alkoxy, acyloxy derived from an alkanoic acid of up to 4 carbon atoms, chlorine, bromine, and iodine, 2,3,4 pyridyl or quinoline, and wherein A represents a member selected from the group consisting of —CO—, —CO—$(CH_2)_n$—CO— wherein $n$ represents an integer of from 1-16, —CO—CH=CH—CO—(cis or trans),

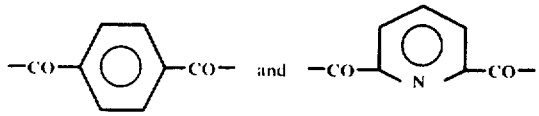

which comprises:
1. Reacting stoichiometric amounts of theophylline with a member selected from the group consisting of the corresponding R-mono-carboxylic acid or anhydride or A-dicarboxylic acid or anhydride, wherein R and A are defined as above, in the presence of:
   a. a solvent selected from the group consisting of a halogenated hydrocarbon solvent and a mixture of said halogenated hydrocarbon solvent with hydrocarbon solvent and/or dimethylformamide,
   b. an excess of a member selected from the group consisting of $COCl_2$ and $SOCl_2$ to yield the desired pro-theophylline compound, said member being present in an amount of from 1.0 to 1.5 equivalents per carboxylic acid group and 1.0 to 2.0 equivalents per anhydride molecule,
   c. about 2 moles of dimethylformamide for each mole of $COCl_2$ or $SOCl_2$,
   d. an inert gas as a carrier or an organic tertiary or aromatic amine base as a scavenger for removing HCl formed during the reaction,
2. Separating the thus obtained pro-theophylline compound from the reaction mixture, said reaction being carried out in an anhydrous environment at a temperature ranging from 0° to 120° C, standard pressure and for a period ranging from 1 to 72 hours.

2. The method of claim 1, wherein said halogenated hydrocarbon solvent is a member selected from the group consisting of dichloromethane, dichloroethane, and chloroform.

3. The method of claim 1, wherein said hydrocarbon solvent is a member selected from the group consisting of benzene, toluene, and xylene.

4. The method of claim 1, wherein said solvent is a mixture of dimethylformamide with a halogenated hydrocarbon solvent.

5. The method of claim 1, wherein said organic tertiary or aromatic amine base is a member selected from the group consisting of trimethylamine, triethylamine, pyridine, methylimidazole, quinoline, quinuclidine, and 2,2-diazabicyclo [2.2.2] octane.

6. The method of claim 1, wherein said reaction is carried out at the boiling point of the solvent or solvent mixture employed.

7. The method of claim 1, wherein the reaction is carried out at a period of time ranging from 20 to 48 hours.

8. The method of claim 1, further comprising the step of purifying the pro-drug theophylline compound by trituration with a hot halogenated hydrocarbon solvent.

9. The method of claim 1, wherein said inert gas is a member selected from the group consisting of nitrogen, helium and purified methane.

* * * * *